United States Patent
Goldman

(10) Patent No.: US 9,724,285 B1
(45) Date of Patent: Aug. 8, 2017

(54) USE OF STABILIZED VITAMIN B-6 (PYRIDOXINE CYCLIC PHOSPHATE) IN CONJUNCTION WITH SKIN COSMETICS

(71) Applicant: Skindinavia, Inc., Scottsdale, AZ (US)

(72) Inventor: Allen Goldman, Scottsdale, AZ (US)

(73) Assignee: Skindinavia, Inc., Scottsdale, AZ (US)

( * ) Notice: Subject to any disclaimer, the term of this patent is extended or adjusted under 35 U.S.C. 154(b) by 0 days.

(21) Appl. No.: 14/333,218

(22) Filed: Jul. 16, 2014

Related U.S. Application Data

(60) Provisional application No. 61/847,378, filed on Jul. 17, 2013.

(51) Int. Cl.
*A61K 8/55* (2006.01)
*A61Q 19/00* (2006.01)

(52) U.S. Cl.
CPC ............... *A61K 8/55* (2013.01); *A61Q 19/00* (2013.01)

(58) Field of Classification Search
CPC .................................. A61K 8/55; A61Q 19/00
See application file for complete search history.

(56) References Cited

U.S. PATENT DOCUMENTS

| | | | | |
|---|---|---|---|---|
| 4,367,227 A | * | 1/1983 | Bingham | A61K 8/63 424/47 |
| 5,415,861 A | * | 5/1995 | Duffy | A61K 8/368 424/401 |
| 5,945,111 A | * | 8/1999 | Esser | B05B 5/025 424/401 |
| 6,403,110 B1 | * | 6/2002 | Siddiqui | A61K 8/27 424/401 |
| 8,003,615 B2 | | 8/2011 | Sakamoto et al. | |
| 8,329,145 B1 | | 12/2012 | Goldman | |
| 2004/0136916 A1 | | 7/2004 | Garrison | |
| 2006/0110353 A1 | | 5/2006 | Rollat-Corvol et al. | |
| 2008/0069898 A1 | * | 3/2008 | Smith | A61K 8/922 424/642 |

OTHER PUBLICATIONS

Skin care industry perspective by Sumi et al., Jul./Sep. 2012, pp. 48-52.*
Daiichi-Stand D70 in cosmetic Business, 2010.*
SAPAWA Congress of 2012.*
Label from a product on sale in Jan. 2007.
Panadoxine TM P Pyridoxine Cyclic Phosphate, 2010.

* cited by examiner

*Primary Examiner* — Blessing M Fubara
(74) *Attorney, Agent, or Firm* — Pandiscio & Pandiscio

(57) ABSTRACT

A composition for reducing sebum production in the skin of a user, the composition comprising:
  a liquid carrier; and
  Pyridoxine Cyclic Phosphate;
  wherein the Pyridoxine Cyclic Phosphate is present in the composition in a concentration sufficient to reduce sebum production in the skin of a user when the composition is applied to the skin of a user.

15 Claims, No Drawings

USE OF STABILIZED VITAMIN B-6 (PYRIDOXINE CYCLIC PHOSPHATE) IN CONJUNCTION WITH SKIN COSMETICS

REFERENCE TO PENDING PRIOR PATENT APPLICATION

This patent application claims benefit of prior U.S. Provisional Patent Application Ser. No. 61/847,378, filed Jul. 17, 2013 by Allen Goldman for USE OF STABILIZED VITAMIN B-6 (PYRIDOXINE CYCLIC PHOSPHATE) IN CONJUNCTION WITH SKIN COSMETICS, which patent application is hereby incorporated herein by reference.

FIELD OF THE INVENTION

This invention relates to skin cosmetics in general, and more particularly to the use of stabilized Vitamin B-6 (Pyridoxine Cyclic Phosphate) in conjunction with skin cosmetics.

BACKGROUND OF THE INVENTION

Skin cosmetics are well known in the art for enhancing the appearance of the user.

Certain skin conditions can detract from the final result of skin cosmetics. By way of example but not limitation, excess sebum (oil) production can result in undesirable "surface shine" which can detract from the final result of skin cosmetics. In addition, excess sebum (oil) production can lead to the deterioration of skin cosmetics, which can also detract from the final result of skin cosmetics. By way of further example but not limitation, excess pore size and/or skin inflammation can result in "unsmooth" skin, which can also detract from the final result of skin cosmetics.

Current approaches for reducing excess sebum (oil) production include the application of oil absorbers and/or light diffusion materials. These oil absorbers and/or light diffusion materials are typically incorporated into a semi-viscous matrix which is manually applied to the skin. In general, these current approaches of applying oil absorbers and/or light diffusion materials suffer from a lack of effectiveness, inconvenience, incompatability with skin cosmetics, etc.

The present invention provides a new and improved approach for reducing excess sebum (oil) production, and for smoothing the skin (by reducing excess pore size and reducing skin inflammation), so as to enhance the final result of skin cosmetics and thereby enhance the appearance of the user.

SUMMARY OF THE INVENTION

The present invention comprises the use of stabilized Vitamin B6 (Pyridoxine Cyclic Phosphate), in conjunction with skin cosmetics, so as to reduce excess sebum (oil) production and to smooth the skin (by reducing excess pore size and reducing skin inflammation), whereby to enhance the final result of skin cosmetics and thereby enhance the appearance of the user.

In one preferred form of the invention, there is provided a composition for reducing sebum production in the skin of a user, the composition comprising:
 a liquid carrier; and
 Pyridoxine Cyclic Phosphate;
 wherein the Pyridoxine Cyclic Phosphate is present in the composition in a concentration sufficient to reduce sebum production in the skin of a user when the composition is applied to the skin of a user.

In another preferred form of the invention, there is provided a method for reducing sebum production in the skin of a user, the method comprising:
 providing a composition comprising:
 a liquid carrier; and
 Pyridoxine Cyclic Phosphate;
 wherein the Pyridoxine Cyclic Phosphate is present in the composition in a concentration sufficient to reduce sebum production in the skin of a user when the composition is applied to the skin of a user; and
 applying the composition to the skin of a user.

DETAILED DESCRIPTION OF THE PREFERRED EMBODIMENTS

The present invention comprises the use of stabilized Vitamin B6 (Pyridoxine Cyclic Phosphate), in conjunction with skin cosmetics, so as to reduce excess sebum (oil) production and to smooth the skin (by reducing excess pore size and reducing skin inflammation), whereby to enhance the final result of skin cosmetics and thereby enhance the appearance of the user.

More particularly, it has been discovered that Vitamin B6 can help to reduce excess sebum (oil) production and to smooth the skin (by reducing excess pore size and reducing skin inflammation). Among other things, it is believed that Vitamin B6 inhibits the 5a-reductase conversion of testosterone to dihydrotestoserone, which in turn reduces sebum (oil) production. Reduction of sebum (oil) production reduces reflected light and, therefore, perceived shine and pore size. Vitamin B6 is also believed to reduce skin inflammation.

Unfortunately, it has been discovered that normal Vitamin B6 is rapidly destabilized by light and heat, making topical application of normal Vitamin B6 minimally effective.

However, it has also been discovered that stabilized Vitamin B6 (Pyridoxine Cyclic Phosphate) is not rapidly destabilized by heat and light, thus making stabilized Vitamin B6 (Pyridoxine Cyclic Phosphate) ideal for topical application to reduce excess sebum (oil) production and to smooth the skin (by reducing excess pore size and reducing skin inflammation). The present invention takes advantage of this discovery and uses stabilized Vitamin B6 (Pyridoxine Cyclic Phosphate), in conjunction with skin cosmetics, so as to reduce excess sebum (oil) production and to smooth the skin (by reducing excess pore size and reducing skin inflammation), whereby to enhance the final result of skin cosmetics and thereby enhance the appearance of the user.

In one form of the present invention, stabilized Vitamin B6 (Pyridoxine Cyclic Phosphate) is applied to the skin of the user as a primer before the application of skin cosmetics. The stabilized Vitamin B6 (Pyridoxine Cyclic Phosphate) reduces excess sebum (oil) production and smooths the skin (by reducing excess pore size and reducing skin inflammation), whereby to provide a superior skin surface for the subsequent application of skin cosmetics. Once the stabilized Vitamin B6 (Pyridoxine Cyclic Phosphate) primer has been applied to the skin of the user, the skin cosmetics may be applied over the primer. The use of the stabilized Vitamin B6 (Pyridoxine Cyclic Phosphate) primer causes the appearance of the skin cosmetics to be enhanced, since the stabilized Vitamin B6 (Pyridoxine Cyclic Phosphate) reduces excess sebum (oil) production and smooths the skin (by reducing excess pore size and reducing skin inflammation), whereby to provide a superior skin surface for applying the skin cosmetics.

Significantly, inasmuch as the stabilized Vitamin B6 (Pyridoxine Cyclic Phosphate) is resistant to destabilization by heat and light, the effect provided by the stabilized Vitamin B6 (Pyridoxine Cyclic Phosphate) is long lasting, and effectively extends the wear-time of the skin cosmetics.

In one preferred form of the invention, the stabilized Vitamin B6 (Pyridoxine Cyclic Phosphate) primer is applied in spray form to the skin of the user, rather than by manual application. Spray application is generally preferred since it is cleaner, more convenient and reduces the opportunity for cross-contamination. However, manual application (e.g., by hand or brush) may also be used if desired.

The stabilized Vitamin B6 (Pyridoxine Cyclic Phosphate) primer may be used on its own, or with "conventional" skin cosmetics or, if preferred, the stabilized Vitamin B6 (Pyridoxine Cyclic Phosphate) may be used with so-called "cooling" skin cosmetics of the type sold by Skindinavia, Inc. of Chestnut Hill, Mass., USA.

The stabilized Vitamin B6 (Pyridoxine Cyclic Phosphate) primer may comprise stabilized Vitamin B6 (Pyridoxine Cyclic Phosphate) delivered in an aqueous-, alcohol-, or polymer-based delivery system, e.g., the stabilized Vitamin B6 (Pyridoxine Cyclic Phosphate) may be combined with a liquid carrier such as a water-, alcohol- or polymer-based liquid carrier, whereby to form the stabilized Vitamin B6 (Pyridoxine Cyclic Phosphate) primer.

In one preferred form of the invention, the stabilized Vitamin B6 (Pyridoxine Cyclic Phosphate) primer comprises a water-based cosmetically-acceptable compound comprising 0.001% to 4.0% by weight stabilized Vitamin B6 (Pyridoxine Cyclic Phosphate) combined with water. And in one more preferred form of the invention, the stabilized Vitamin B6 (Pyridoxine Cyclic Phosphate) primer comprises a water-based cosmetically-acceptable compound comprising 0.1% to 3.0% by weight stabilized Vitamin B6 (Pyridoxine Cyclic Phosphate) combined with water.

In another preferred form of the invention, the stabilized Vitamin B6 (Pyridoxine Cyclic Phosphate) primer comprises an alcohol-based cosmetically-acceptable compound comprising 0.001% to 4.0% by weight stabilized Vitamin B6 (Pyridoxine Cyclic Phosphate) combined with alcohol. And in one more preferred form of the invention, the stabilized Vitamin B6 (Pyridoxine Cyclic Phosphate) primer comprises an alcohol-based cosmetically-acceptable compound comprising 0.1% to 3.0% by weight stabilized Vitamin B6 (Pyridoxine Cyclic Phosphate) combined with alcohol.

In another preferred form of the invention, the stabilized Vitamin B6 (Pyridoxine Cyclic Phosphate) primer comprises a water- and alcohol-based cosmetically-acceptable compound comprising 0.001% to 4.0% by weight stabilized Vitamin B6 (Pyridoxine Cyclic Phosphate) combined with water and alcohol. And in one more preferred form of the invention, the stabilized Vitamin B6 (Pyridoxine Cyclic Phosphate) primer comprises a water- and alcohol-based cosmetically-acceptable compound comprising 0.1% to 3.0% by weight stabilized Vitamin B6 (Pyridoxine Cyclic Phosphate) combined with water and alcohol.

In another preferred form of the invention, the stabilized Vitamin B6 (Pyridoxine Cyclic Phosphate) primer comprises a polymer-based cosmetically-acceptable compound comprising 0.001% to 4.0% by weight stabilized Vitamin B6 (Pyridoxine Cyclic Phosphate) combined with a liquid polymer. And in one more preferred form of the invention, the stabilized Vitamin B6 (Pyridoxine Cyclic Phosphate) primer comprises a polymer-based cosmetically-acceptable compound comprising 0.1% to 3.0% by weight stabilized Vitamin B6 (Pyridoxine Cyclic Phosphate) combined with a liquid polymer. In one preferred form of the invention, the polymer-based cosmetically-acceptable compound is a polymer gel-based cosmetic compound. One such polymer gel is acrylate/C10-30 alkyl acrylate crosspolymer.

In another preferred form of the invention, the stabilized Vitamin B6 (Pyridoxine Cyclic Phosphate) primer comprises a silicone-based cosmetically-acceptable compound comprising 0.001% to 4.0% by weight stabilized Vitamin B6 (Pyridoxine Cyclic Phosphate) combined with a liquid silicone. And in one more preferred form of the invention, the stabilized Vitamin B6 (Pyridoxine Cyclic Phosphate) primer comprises a silicone-based cosmetically-acceptable compound comprising 0.1% to 3.0% by weight stabilized Vitamin B6 (Pyridoxine Cyclic Phosphate) combined with a liquid silicone.

If desired, fine particulate solids (such as acrylates, silicas or other fine solids) may be incorporated in the stabilized Vitamin B6 (Pyridoxine Cyclic Phosphate) primer to reduce reflectivity.

Furthermore, if desired, isononyl isononanoate or ethylhexyl isononanoate (which is used to cool the surface of the skin) may be incorporated in the stabilized Vitamin B6 (Pyridoxine Cyclic Phosphate) primer.

Furthermore, if desired, anti-acne ingredients may be incorporated in the stabilized Vitamin B6 (Pyridoxine Cyclic Phosphate) primer. By way of example but not limitation, *Salix Nigra* (Willow Bark) Extract, Benzoyl Peroxide and/or Salycilic Acid may be incorporated in the stabilized Vitamin B6 (Pyridoxine Cyclic Phosphate) primer.

In one preferred form of the invention, the stabilized Vitamin B6 (Pyridoxine Cyclic Phosphate) primer comprises water, stabilized Vitamin B6 (Pyridoxine Cyclic Phosphate), Acrylates/C10-30 Alkyl Acrylates Crosspolymer, Sodium Hydroxide, Phenoxyethanol, Ethylhexylglycerin, and a coloring agent, e.g., Blue 1 (Cl 42090).

In one preferred form of the invention, the stabilized Vitamin B6 (Pyridoxine Cyclic Phosphate) primer comprises:

| Chemical Name (INCI) | % Active Composition by weight |
| --- | --- |
| Water (Aqua) | 88-92% |
| Alcohol Denat | 3-6% |
| Hydrolyzed Corn Starch | 1-2% |
| Phenoxyethanol | .5-1% |
| Propanediol | .5-1% |
| Xylitol Phosphate Esters | .25-.50% |
| Polyhydroxystearic Acid | .25-.50% |
| *Salix Nigra* (Willow) Bark Extract | .25-.50% |
| Menthyl Ethylamido Oxalate | .25-.50% |
| Glycereth-5 Lactate | .1-.25% |
| Xylitol | .1-.25% |
| Ethylhexyl Isononanoate | .1-.25% |
| Isononyl Isononanoate | .1-.25% |
| *Aloe Barbadensis* Leaf Extract | .1-.25% |
| Pyridoxine Cyclic Phosphate | .0001-4% |
| Panthenol | .0001-4% |
| Silica | .1-.25% |
| Ethylhexylglycerin | .01-.15% |
| Sodium Cocamidopropyl PG-Dimonium Chloride Phosphate | .01-.15% |
| Tocopheryl Acetate | .01-.15% |
| Hydrolyzed Soy Protein | .01-.15% |
| Fructan | .01-.15% |
| Sodium Hydroxide | .01-.15% |
| Methyl Diisopropyl Propionamide | .01-.15% |
| Butylene Glycol | .01-.15% |
| Fragrance (Parfum) | .01-.15% |
| Coconut Acid | .01-.15% |
| TOTAL: | 100.000 |

In one preferred method for applying the stabilized Vitamin B6 composition to the skin of a user, a user may use a "fine mist" pump-type sprayer to apply the composition to the surface of the skin in a uniform manner. The "fine mist" pump sprayer causes the liquid to be deployed as fine particles or droplets, with the fine particles or droplets comprising part of an air stream that is directed toward the user's skin surface. In one preferred form of the invention, the droplets preferably range in size from about 20 microns up to about 150 microns.

Among other advantages, applying a uniform fine mist of the composition to the surface of the skin is more comfortable for a user because the small particle size results in less conductive cooling than large liquid droplets striking the skin. Large liquid droplets can also make a user's skin feel "wet".

Further, and significantly, applying the composition to the skin as a fine mist distributes the active ingredients more evenly than they would otherwise be distributed if the composition were applied using larger droplets. Application of larger droplets can result in an uneven delivery of the ingredients (e.g., the ingredients may be delivered as "clumps" in localized concentrated locations). In the case of cosmetics, such uneven distribution can appear as blotches or uneven pigmentation, or provide undesirable reflectivity.

In addition, if desired, stabilized Vitamin B6 (Pyridoxine Cyclic Phosphate) may be incorporated directly into the skin cosmetics themselves, rather than applied to the skin as a separate primer prior to the application of the skin cosmetics.

MODIFICATIONS

While the present invention has been described in terms of certain exemplary preferred embodiments, it will be readily understood and appreciated by those skilled in the art that it is not so limited, and that many additions, deletions and modifications may be made to the preferred embodiments discussed herein without departing from the scope of the invention.

What is claimed is:

1. A method for reducing sebum production in the skin of a user, the method comprising:
   providing a composition comprising:
     a liquid carrier;
     Pyridoxine Cyclic Phosphate;
     wherein the Pyridoxine Cyclic Phosphate is present in the composition in a concentration sufficient to reduce sebum production in the skin of a user when the composition is applied to the skin of a user;
     water in a concentration of 88-92% by weight;
     denatured alcohol in a concentration of 3-6% by weight;
     Hydrolyzed Corn Starch in a concentration of 1-2% by weight;
     Phenoxyethanol in a concentration of 0.5-1% by weight;
     Propanediol in a concentration of 0.5-1% by weight;
     Xylitol Phosphate Esters in a concentration of 0.25-0.50% by weight;
     Polyhydroxystearic Acid in a concentration of 0.25-0.50% by weight;
     *Salix Nigra* (Willow) Bark Extract in a concentration of 0.25-0.50% by weight;
     Menthyl Ethylamido Oxalate in a concentration of 0.25-0.50% by weight;
     Glycereth-5 Lactate in a concentration of 0.1-0.25% by weight;
     Xylitol in a concentration of 0.1-0.25% by weight;
     Ethylhexyl Isononanoate in a concentration of 0.1-0.25% by weight;
     Isononyl Isononanoate in a concentration of 0.1-0.25% by weight;
     Aloe Barbadensis Leaf Extract in a concentration of 0.1-0.25% by weight;
     Pyridoxine Cyclic Phosphate in a concentration of 0.0001-4% by weight;
     Panthenol in a concentration of 0.0001-4% by weight;
     Silica in a concentration of 0.1-0.25% by weight;
     Ethylhexylglycerin in a concentration of 0.01-0.15% by weight;
     Sodium Cocamidopropyl PG-Dimonium Chloride Phosphate in a concentration of 0.01-0.15% by weight;
     Tocopheryl Acetate in a concentration of 0.01-0.15% by weight;
     Hydrolyzed Soy Protein in a concentration of 0.01-0.15% by weight;
     Fructan in a concentration of 0.01-0.15% by weight;
     Sodium Hydroxide in a concentration of 0.01-0.15% by weight;
     Methyl Diisopropyl Propionamide in a concentration of 0.01-0.15% by weight;
     Butylene Glycol in a concentration of 0.01-0.15% by weight;
     Fragrance (Parfum) in a concentration of 0.01-0.15% by weight; and
     Coconut Acid in a concentration of 0.01-0.15% by weight; and
   applying the composition to the skin of a user.

2. A method for reducing sebum production in the skin of a user, the method comprising:
   providing a composition comprising:
     water in a concentration of 88-92% by weight;
     denatured alcohol in a concentration of 3-6% by weight;
     Hydrolyzed Corn Starch in a concentration of 1-2% by weight;
     Phenoxyethanol in a concentration of 0.5-1% by weight;
     Propanediol in a concentration of 0.5-1% by weight;
   Xylitol Phosphate Esters in a concentration of 0.25-0.50% by weight;
     Polyhydroxystearic Acid in a concentration of 0.25-0.50% by weight;
     *Salix Nigra* (Willow) Bark Extract in a concentration of 0.25-0.50% by weight;
     Menthyl Ethylamido Oxalate in a concentration of 0.25-0.50% by weight;
     Glycereth-5 Lactate in a concentration of 0.1-0.25% by weight;
     Xylitol in a concentration of 0.1-0.25% by weight;
     Ethylhexyl Isononanoate in a concentration of 0.1-0.25% by weight;
     Isononyl Isononanoate in a concentration of 0.1-0.25% by weight;
     Aloe Barbadensis Leaf Extract in a concentration of 0.1-0.25% by weight;
     Pyridoxine Cyclic Phosphate in a concentration of 0.0001-4% by weight;
     Panthenol in a concentration of 0.0001-4% by weight;
     Silica in a concentration of 0.1-0.25% by weight,
     Ethylhexylglycerin in a concentration of 0.01-0.15% by weight;

Sodium Cocamidopropyl PG-Dimonium Chloride Phosphate in a concentration of 0.01-0.15% by weight;

Tocopheryl Acetate in a concentration of 0.01-0.15% by weight;

Hydrolyzed Soy Protein in a concentration of 0.01-0.15% by weight;

Fructan in a concentration of 0.01-0.15% by weight;

Sodium Hydroxide in a concentration of 0.01-0.15% by weight;

Methyl Diisopropyl Propionamide in a concentration of 0.01-0.15% by weight;

Butylene Glycol in a concentration of 0.01-0.15% by weight;

Fragrance (Parfum) in a concentration of 0.01-0.15% by weight; and

Coconut Acid in a concentration of 0.01-0.15% by weight; and applying the composition to the skin of a user.

3. A method for reducing sebum production in the skin of a user, the method comprising:

providing a composition comprising:
    a liquid carrier; and
    Pyridoxine Cyclic Phosphate;
    wherein the Pyridoxine Cyclic Phosphate is present in the composition in a concentration sufficient to reduce sebum production in the skin of a user when the composition is applied to the skin of a user;
    wherein the liquid carrier comprises water, and the composition further comprises Acrylates/C10-30 Alkyl Acrylates Crosspolymer, Sodium Hydroxide, Phenolxyethanol, Ethylhexylglycerin and Blue 1 (Cl 42090); and applying the composition to the skin of a user.

4. A method according to claim 3 wherein the composition comprises 0.001%-4.0% by weight Pyridoxine Cyclic Phosphate.

5. A method according to claim 3 wherein the composition comprises 0.1%-3.0% by weight Pyridoxine Cyclic Phosphate.

6. A method according to claim 3 wherein the liquid carrier comprises a water-based compound.

7. A method according to claim 3 wherein the liquid carrier comprises an alcohol-based compound.

8. A method according to claim 3 wherein the liquid carrier comprises a water and alcohol-based compound.

9. A method according to claim 3 wherein the composition further comprises fine particulate solids.

10. A method according to claim 3 wherein the composition further comprises compounds which provide a cooling effect on the surface of the skin of the user.

11. A method according to claim 3 wherein the composition further comprises anti-acne ingredients.

12. A method according to claim 3 wherein the composition further comprises a cosmetic.

13. A method according to claim 3 wherein the composition is applied to the skin of the user as a fine mist.

14. A method according to claim 13 wherein the fine mist comprises droplets of the composition sized between 40 microns and 150 microns.

15. A method according to claim 3 further comprising applying a cosmetic over the composition applied to the skin of the user.

* * * * *